(12) United States Patent
Herweck et al.

(10) Patent No.: US 8,574,618 B2
(45) Date of Patent: Nov. 5, 2013

(54) PERFORATED BIOABSORBABLE OIL FILM AND METHODS FOR MAKING THE SAME

(71) Applicant: Atrium Medical Corporation, Hudson, NH (US)

(72) Inventors: Steve A. Herweck, Wellesley, MA (US); Thomas M. Swanick, Hillsborough, NH (US); Joseph Ferraro, Londonderry, NH (US); Paul Martakos, Pelham, NH (US); Lisa Rogers, Londonderry, NH (US); Theodore Karwoski, Hollis, NH (US); Keith M. Faucher, Nashua, NH (US); Philip McNamara, Concord, NH (US); Roger Labrecque, Londonderry, NH (US); Suzanne Conroy, Dracut, MA (US); Trevor Carlton, Hudson, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 13/682,991

(22) Filed: Nov. 21, 2012

(65) Prior Publication Data

US 2013/0074452 A1     Mar. 28, 2013

Related U.S. Application Data

(63) Continuation of application No. 11/525,390, filed on Sep. 22, 2006, now Pat. No. 8,367,099, which is a continuation-in-part of application No. 11/237,264, filed on Sep. 28, 2005.

(60) Provisional application No. 60/613,808, filed on Sep. 28, 2004, provisional application No. 60/726,869, filed on Oct. 14, 2005.

(51) Int. Cl.
*A61F 2/02*     (2006.01)

(52) U.S. Cl.
USPC .......................................................... 424/423

(58) Field of Classification Search
None
See application file for complete search history.

(56) References Cited

U.S. PATENT DOCUMENTS

| 3,556,294 A | 1/1971 | Walck et al. |
| 3,967,728 A | 7/1976 | Gordon et al. |

(Continued)

FOREIGN PATENT DOCUMENTS

| EP | 0471566 | 2/1992 |
| EP | 0610731 | 8/1994 |

(Continued)

OTHER PUBLICATIONS

Autosuture, "ParietexTM Composite OS Series Mesh," retrieved online at http://www.autosuture.com/AutoSuture/pagebuilder.aspx?topicID=135734&breadcrumbs=135 601:0 (2007).

(Continued)

*Primary Examiner* — Carlos Azpuru
(74) *Attorney, Agent, or Firm* — Morse, Barnes-Brown & Pendelton, P.C.; Sean D. Detweiler, Esq.

(57) ABSTRACT

A bio-absorbable stand-alone film is derived at least in part from fatty acids. The bio-absorbable stand-alone film can have anti-adhesive, anti-inflammatory, non-inflammatory, and wound healing properties, and can additionally include one or more therapeutic agents incorporated therein. The stand-alone film has one or more perforations or depressions formed therein. Corresponding methods of making the bio-absorbable stand-alone film with one or more perforations or depressions include molding, cutting, carving, puncturing or otherwise suitable methods to create the perforations or depressions in the bio-absorbable stand-alone film. The resulting stand-alone film is bioabsorbable.

17 Claims, 11 Drawing Sheets

(56) References Cited

U.S. PATENT DOCUMENTS

| | | |
|---|---|---|
| 4,308,120 A | 12/1981 | Pennewiss et al. |
| 4,323,547 A | 4/1982 | Knust et al. |
| 4,664,114 A | 5/1987 | Ghodstain |
| 4,813,210 A | 3/1989 | Masuda et al. |
| 4,814,329 A | 3/1989 | Harsanyi et al. |
| 4,847,301 A | 7/1989 | Murray |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,941,308 A | 7/1990 | Grabenkort et al. |
| 4,968,302 A | 11/1990 | Schluter et al. |
| 5,017,229 A | 5/1991 | Burns et al. |
| 5,147,374 A | 9/1992 | Fernandez |
| 5,151,272 A | 9/1992 | Engstrom et al. |
| 5,171,148 A | 12/1992 | Wasserman et al. |
| 5,179,174 A | 1/1993 | Elton |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,403,283 A | 4/1995 | Luther |
| 5,447,940 A | 9/1995 | Harvey et al. |
| 5,464,650 A | 11/1995 | Berg et al. |
| 5,480,653 A | 1/1996 | Aguadisch et al. |
| 5,509,899 A | 4/1996 | Fan et al. |
| 5,579,149 A | 11/1996 | Moret et al. |
| 5,580,923 A | 12/1996 | Yeung et al. |
| 5,591,230 A | 1/1997 | Horn et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,736,152 A * | 4/1998 | Dunn ............................ 424/426 |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,015,844 A | 1/2000 | Harvey et al. |
| 6,028,164 A | 2/2000 | Loomis |
| 6,040,330 A | 3/2000 | Hausheer et al. |
| 6,056,970 A | 5/2000 | Greenawalt et al. |
| 6,077,698 A | 6/2000 | Swan et al. |
| 6,083,950 A | 7/2000 | Anand et al. |
| 6,090,809 A | 7/2000 | Anand et al. |
| 6,117,911 A | 9/2000 | Grainger et al. |
| 6,120,789 A | 9/2000 | Dunn |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,491,938 B2 | 12/2002 | Kunz et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim et al. |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,415,811 B2 | 8/2008 | Gottlieb et al. |
| 8,124,127 B2 | 2/2012 | Faucher et al. |
| 8,263,102 B2 | 9/2012 | Labrecque et al. |
| 8,312,836 B2 | 11/2012 | Corbeil et al. |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0032414 A1 | 3/2002 | Ragheb et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |

(56) References Cited

U.S. PATENT DOCUMENTS

| | | |
|---|---|---|
| 2003/0069632 A1 | 4/2003 | De Scheerder et al. |
| 2003/0072784 A1 | 4/2003 | Williams |
| 2003/0077272 A1 | 4/2003 | Pathak |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0071756 A1 | 4/2004 | Fischell et al. |
| 2004/0073284 A1 | 4/2004 | Bates et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0230176 A1 | 11/2004 | Shanahan et al. |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0158361 A1 | 7/2005 | Dhondt et al. |
| 2005/0159809 A1 | 7/2005 | Hezi-Yamit et al. |
| 2005/0182485 A1 | 8/2005 | Falotico et al. |
| 2005/0187376 A1 | 8/2005 | Pacetti |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0212411 A1 | 9/2007 | Fawzy et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0044481 A1 | 2/2008 | Harel |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0206305 A1 | 8/2008 | Herweck et al. |
| 2008/0279929 A1 | 11/2008 | Devane et al. |
| 2008/0286440 A1 | 11/2008 | Scheer |
| 2009/0011116 A1 | 1/2009 | Herweck et al. |
| 2009/0047414 A1 | 2/2009 | Corbeil et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 1402906 | 6/2011 |
| WO | WO 86/00912 | 2/1986 |
| WO | WO 90/01969 | 3/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | WO 98/54275 | 12/1998 |
| WO | WO 99/25336 | 5/1999 |
| WO | WO-00/40278 | 7/2000 |
| WO | WO-00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO-02/100455 | 12/2002 |
| WO | WO-03/000308 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO-03/039612 | 5/2003 |
| WO | WO 03/041756 | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | WO 2008/057328 | 5/2008 |
| WO | WO 2012/009707 | 1/2012 |

(56) References Cited

FOREIGN PATENT DOCUMENTS

OTHER PUBLICATIONS

Binder et al., "Chromatographic Analysis of Seed Oils. Fatty Acid Composition of Castor Oil," The Journal of the American Oil Chemists' Society, vol. 39:513-517 (1962).
Redman, L.V. et al., "The drying rate of raw paint oils—a comparison," The Journal of Industrial and Engineering Chemistry, vol. 5: 630-636 (1913).
Drummond, Calum J., et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei, et al, "Physiological Transport Forces Govern Drug Distribution for Stent-Based Delivery," Circulation, vol. 104:600-605 (2001).
Mallegol, et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin, et al, "Local and Systemic Delivery of Low Molecular Weight Heparin Following PTCA: Acute Results and 6-Month Follow-Up of the Initial Clinical Experience With the Porous Balloon (Pilot-Study)," Catheterization and Cardiovascular Diagnosis, vol. 44:267-274 (1998).
Salu, Koen J., et al, "Addition of cytochalasin D to a biocompatible oil stent coating inhibits intimal hyperplasia in a porcine coronary model," Coronary Artery Disease, vol. 14(8):545-555 (2003).
Scheller, Bruno, et al, "Addition of Paclitaxel to Contrast Media Prevents Restenosis After Coronary Stent Implantation," Journal of the American College of Cardiology, vol. 42(8):1415-1420 (2003).
Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).
Ogunniyi, D.S., "Castor oil: A vital industrial raw material," Biosource Technology, vol. 97: 1086-1091 2006.
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Timir-Balizsy et al., "Chemical Principals of Textile Conservation," Oxford: Elsevier Science Ltd., 1998:117-119.
"Polymerization" Merriam-Webster Online Dictionary, retrieved from <www.merriam-webster.com> on Dec. 13, 2009; Merriam-Webster's Inc. 2009; pp. 1.
Shahidi, Fereidoon ed.; "Bailey's Industrial Oil and Fats Products" 2005; John Wiley and Sons; vol. 5, Edible Oil and Fat Products: Processing Technologies, pp. 1-15.
Ahtia et al. Journal of Indian Pediatric Surgery 2002 7:15-20.
Jonasson, Lena et al., "Cyclosporon A inhibits smooth muscle proliferation in the vascular response to injury," Proc. Natl. Acad. Sci. USA, vol. 85: 2303-2306 (1988).
Wikipedia, "Sirolimus," pp. 1-13, available online at http://en.wikipedia.org/wiki/Sirolimus, date accessed May 11, 2011.
CECW-EE, "Ch. 4: Coating Types and Characteristics," Engineering and Design—Painting: New Construction and Maintenance, pp. 4-1 to 4-24 (1995).
Rutkow, Ira M. et al., "'Tension-free' inguinal herniorrhaphy: A preliminary report on the 'mesh plug' technique," Surgery, vol. 114:3-8 (1993).
Websters Dictionary Online, Accessed on Feb. 13, 2009, entry for "polymer" p. 1 of 1.
International Search Report for International Application PCT/US05/034601, dated Apr. 10, 2006.

International Search Report for International Application PCT/US05/034610, dated Mar. 16, 2006.
International Search Report for International Application PCT/US05/034614, dated Aug. 29, 2006.
International Search Report for International Appl cat on PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Applicat on PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007,.
International Search Report for International Application PCT/US07/019978, dated May 7, 2009,.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
International Search Report for International Application No. PCT/U805/34941, dated May 4, 2006.
Supplementary European Search Report for Application No, EP 08877338.7, dated Aug. 16, 2012.
Supplementary European Search Report for Application No. EP09819594.4, dated Aug. 14, 2012.
International Search Report for PCT/US2011/44292, dated Dec. 6, 2011.
Non-final Office Action for U.S. Appl. No. 11/236,908 (listed on SB/08 as US 2006/0067974), mailed Mar. 25, 2006.
Final Office Action for U.S. Appl. No. 11/236,908 (listed on SB/08 as US 2006/0067974), mailed May 17, 2011.
Non-final Office Action for U.S. Appl. No. 11/236,908 (listed on SB/08 as US 2006/0067974), mailed Aug. 24, 2009.
Non-final Office Action for U.S. Appl. No. 11/236,977 (listed on SB/08 as US 2006/0088596), mailed Aug. 3, 2009.
Final Office Action for U.S. Appl. No. 11/237,263 (listed on SB/08 as US 2006/0110457), mailed Jul. 7, 2010.
Non-final Office Action for U.S. Appl. No. 11/237,263 (listed on SB/08 as US 2006/0110457), mailed Oct. 7, 2009.

(56) References Cited

OTHER PUBLICATIONS

Final Office Action for U.S. Appl. No. 11/237,264 (listed on SB/08 as US 2006/0067983), mailed Jun. 2, 2010.
Non-final Office Action for U.S. Appl. No. 11/237,264 (listed on SB/08 as US 2006/0067983), mailed Oct. 5, 2009.
Final Office Action for U.S. Appl. No. 11/701,799 (listed on SB/08 as US 2008/0109017), mailed Nov. 23, 2010.
Non-final Office Action for U.S. Appl. No. 11/237,420 (listed on SB/08 as US 2006/0078586), mailed Mar. 5, 2009.
Final Office Action for U.S. Appl. No. 11/237,420 (listed on SB/08 as US 2006/0078586), mailed Nov. 4, 2009.
Non-final Office Action for U.S. Appl. No. 11/237,420 (listed on SB/08 as US 2006/0078586), mailed Dec. 6, 2010.
Non-final Office Action for U.S. Appl. No. 11/238,532 (listed on SB/08 as US 2006/0067976), mailed Mar. 30, 2009.
Final Office Action for U.S. Appl. No. 11/238,532 (listed on SB/08 as US 2006/0067976), mailed Sep. 9, 2009.
Final Office Action for U.S. Appl. No. 11/238,554, (listed on SB/08 as US 2006/0121081), mailed May 12, 2010.
Non-final Office Action for U.S. Appl. No. 11/238,554 (listed on SB/08 as US 2006/0121081), mailed Oct. 9, 2009.
Final Office Action for U.S. Appl. No. 11/238,554 (listed on SB/08 as US 2006/0121081), mailed May 1, 2009.
Non-final Office Action for U.S. Appl. No. 11/238,554 (listed on SB/08 as US 2006/0121081), mailed Jul. 25, 2008.
Non-final Office Action for U.S. Appl. No. 11/238,564 (listed on SB/08 as US 2006/0083768), mailed Apr. 16, 2008.
Final Office Action for U.S. Appl. No. 11/238,564 (listed on SB/08 as US 2006/0083768), mailed Aug. 6, 2009.
Non-final Office Action for U.S. Appl. No. 11/239,555 (listed on SB/08 as US 2006/0067977), mailed Mar. 30, 2009.
Non-final Office Action for U.S. Appl. No. 11/525,328 (listed on SB/08 as US 2007/0084144), mailed Apr. 30, 2007.
Non-final Office Action for U.S. Appl. No. 11/525,390 (listed on SB/08 as US 2007/0071798), mailed Jul. 14, 2010.
Final Office Action for U.S. Appl. No. 11/525,390 (listed on SB/08 as US 2007/0071798), mailed Feb. 21, 2011.
Final Office Action for U.S. Appl. No. 11/582,135 (listed on SB/08 as US 2007/0202149), mailed May 12, 2011.
Non-final Office Action for U.S. Appl. No. 11/582,135 (listed on SB/08 as US 2007/0202149), mailed Nov. 9, 2010.
Non-final Office Action for U.S. Appl. No. 11/582,135 (listed on SB/08 as US 2007/0202149), mailed Jan. 6, 2010.
Non-final Office Action for U.S. Appl. No. 11/582,135 (listed on SB/08 as US 2007/0202149), mailed May 12, 2009.
Non-final Office Action for U.S. Appl. No. 11/701,799 (listed on SB/08 as US 2008/0109017), mailed Apr. 12, 2010.
Non-final Office Action for U.S. Appl. No. 11/978,840 (listed on SB/08 as US 2008/0118550), mailed Dec. 3, 2010.
Non-final Office Action for U.S. Appl. No. 11/980,155 (listed on SB/08 as US 2008/0113001), mailed Mar. 24, 2011.
Non-final Office Action for U.S. Appl. No. 12/075,223 (listed on SB/08 as US 2008/0206305), mailed Dec. 8, 2010.
Non-final Office Action for U.S. Appl. No. 12/325,546 (listed on SB/08 as US 2009/0181937), mailed Feb. 25, 2010.
Final Office Action for U.S. Appl. No. 12/325,546 (listed on SB/08 as US 2009/0181937), mailed Aug. 31, 2010.
Non-final Office Action for U.S. Appl. No. 12/364,763 (listed on SB/08 as US 2009/0208552), mailed Dec. 11, 2009.
Final Office Action for U.S. Appl. No. 12/364,763 (listed on SB/08 as US 2009/0208552), mailed Sep. 21, 2010.
Interview summary for U.S. Appl. No. 11/236,908 (listed on SB/08 as US 2006/0067974) mailed May 5, 2009.
Interview summary for U.S. Appl. No. 11/236,908 (listed on SB/08 as US 2006/0067974) mailed Dec. 2, 2010.
Interview summary for U.S. Appl. No. 11/237,420 (listed on SB/08 as US 2006/0078586) mailed May 5, 2009.
Interview summary for U.S. Appl. No. 11/582,135 (listed on SB/08 as US 2007/0202149) mailed Dec. 7, 2010.
Interview summary for U.S. Appl. No. 12/325,546 (listed on SB/08 as US 2009/0181937) mailed Dec. 2, 2010.
Interview summary for U.S. Appl. No. 12/364,763 (listed on SB/08 as US 2009/0208552) mailed Dec. 2, 2010.
Final Office Action for U.S. Appl. No. 11/237,420 (listed on SB/08 as US 2006/0078586), mailed Jul. 13, 2011.
Final Office Action for U.S. Appl. No. 11/978,840 (listed on SB/08 as US 2008/0118550), mailed Jun. 22, 2011.
Final Office Action for U.S. Appl. No. 12/075,223 (listed on SB/08 as US 2008/0206305), mailed Aug. 11, 2011.
Non-final Office Action for U.S. Appl. No. 11/525,390 (listed on SB/08 as US 2007/0071798), mailed Jul. 11, 2011.
Non-Final Office Action for U.S. Appl. No. 11/701,799 (listed on SB/08 as US 2008/0109017), mailed Aug. 17, 2011.
Non-Final Office Action for U.S. Appl. No. 11/582,135 (listed on SB/08 as US-2007-0202149), mailed Oct. 14, 2011.
Final Office Action for U.S. Appl. No. 11/980,155 (listed on SB/08 as US-2008-0113001), mailed Oct. 21, 2011.
Non-Final Office Action for U.S. Appl. No. 11/236,908 (listed on SB/08 as US-2006-0067974), mailed Dec. 2, 2011.
Non-Final Office Action for U.S. Appl. No. 12/182,261 (listed on SB/08 as US 2009-0047414), mailed Dec. 21, 2011.
Non-Final Office Action for U.S. Appl. No. 12/401,243 (listed on SB/08 as US 2010-0233232), mailed Jan. 5, 2012.
Notice of Allowance for U.S. Appl. No. 11/582,135 (listed on SB/08 as US 2007-0202149), mailed Jan. 9, 2012.
Non-Final Office Action for U.S. Appl. No. 12/182,165 (listed on SB/08 as US 2009-0011116), mailed Jan. 5, 2012.
Final Office Action for U.S. Appl. No. 11/701,799 (listed on SB/08 as US 2008/0109017), mailed Feb. 13, 2012.
Non-Final Office Action for U.S. Appl. No. 12/581,582 (listed on SB/08 as US 20100183697), mailed Mar. 14, 2012.
Final Office Action for U.S. Appl. No. 12/182,165 (listed on SB/08 as US 2009-0011116), mailed Apr. 6, 2012.
Final Office Action for U.S. Appl. No. 12/182,261 (listed on SB-08 as US 2009/0047414) mailed Apr. 30, 2012.
Notice of Allowance for U.S. Appl. No. 11/236,908 (listed on SB/08 as US-2006-0067974), mailed May 11, 2012.
Final Office Action for U.S. Appl. No. 12/401,243 (listed on SB/08 as US- 2010-0233232), mailed Jun. 11, 2012.
Notice of Allowance for U.S. Appl. No. 12/182,261 (listed on SB/08 as US-2009/0047414), mailed Jul. 23, 2012.
Advisory Action for U.S. Appl. No. 12/401,243 (listed on SB/08 as US 2010-0233232), mailed Aug. 27, 2012.
Final Office Action for U.S. Appl. No. 12/581,582 (listed on SB-08 as US 2010/0183697) mailed Aug. 29, 2012.
Notice of Allowance for U.S. Appl. No. 11/525,390 (listed on SB/08 as US-2007/0071798), mailed Oct. 4, 2012.
Final Office Action for U.S. Appl. No. 11/236,943 (listed on SB/08 as US 2006/0067975), mailed Dec. 23, 2009.
Non-Final Office Action for U.S. Appl. No. 11/236,943 (listed on SB/08 as US 2006/0067975), mailed Mar. 5, 2009.
Advisory Action for U.S. Appl. No. 12/581,582 (listed on SB/08 as US 2010-0183697), mailed Nov. 14, 2012.

\* cited by examiner

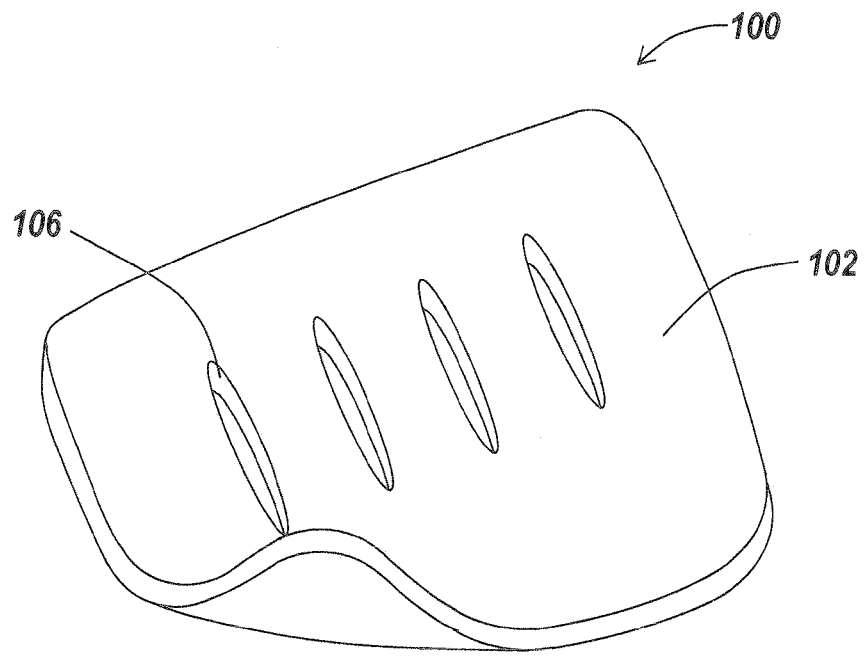
*Fig. 1A*
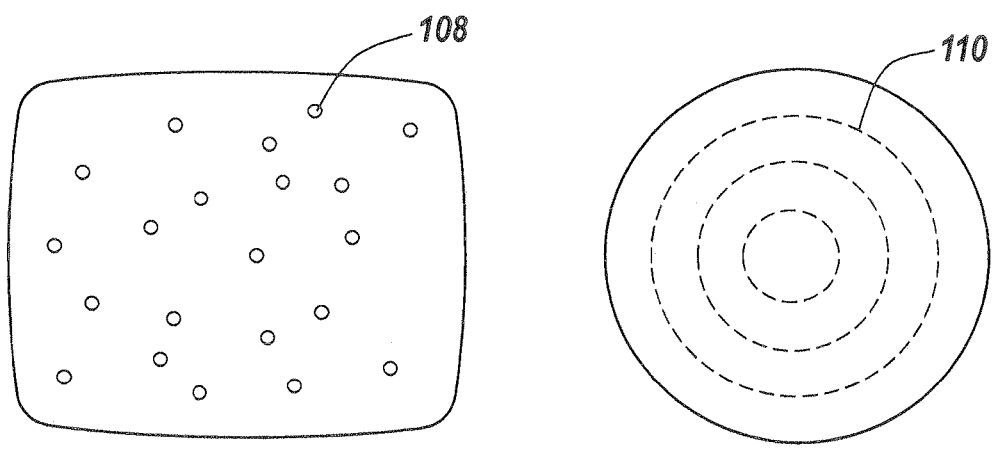
*Fig. 1B*     *Fig. 1C*

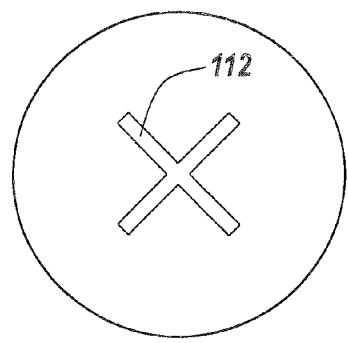
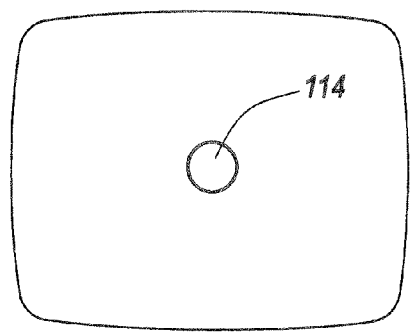
Fig. 1D    Fig. 1E
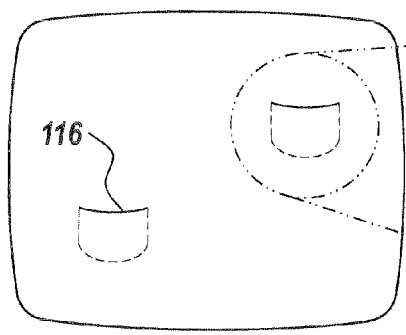
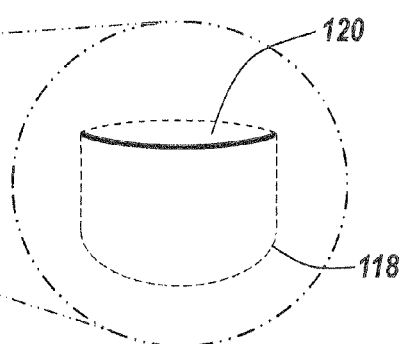
Fig. 1F
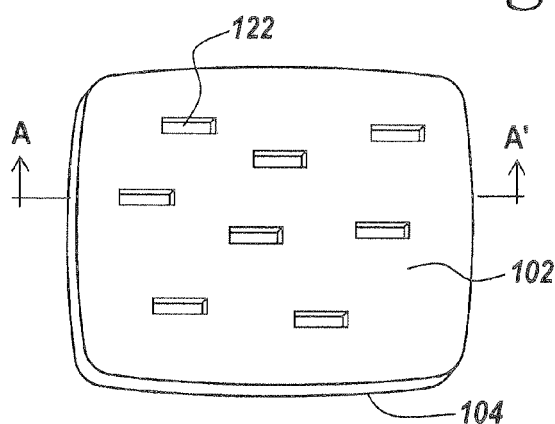
Fig. 1G    Fig. 1H

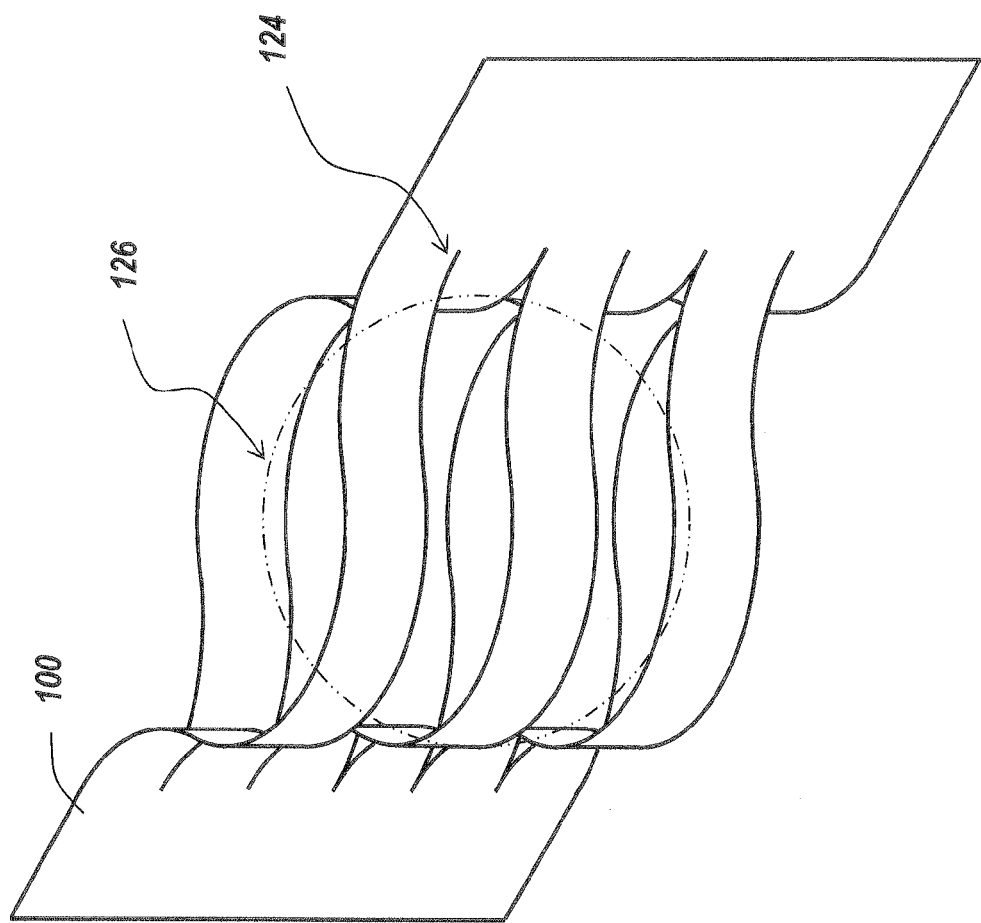

PERFORATED BIOABSORBABLE OIL FILM AND METHODS FOR MAKING THE SAME

RELATED APPLICATIONS

This application is a continuation of co-pending U.S. patent application Ser. No. 11/525,390, filed on Sep. 22, 2006, which is a continuation in part of U.S. patent application Ser. No. 11/237,264, filed on Sep. 28, 2005, which claims priority to, and the benefit of, U.S. Provisional Application No. 60/613,808, filed on Sep. 28, 2004, and which also claims priority to U.S. Provisional Application No. 60/726,869, filed Oct. 14, 2005. The disclosures of the above-mentioned applications are hereby incorporated by reference herein in their entirety.

FIELD OF THE INVENTION

The present invention generally relates to bioabsorbable bio-absorbable stand-alone films, and more particularly to perforated bioabsorbable bio-absorbable stand-alone films.

BACKGROUND OF THE INVENTION

Different surgical procedures often make use of a method referred to as blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colo-rectal, urology, gynecology, upper GI, and plastic surgery applications, among others.

In accordance with several methods of blunt dissection, a small incision is made in the patient. Specially designed blunt dissection tools having small profiles are inserted through the incision to the desired location in the body. Longer tools may be used to access locations substantially distal from the incision, while shorter tools can be used to access locations closer to the incision.

After the blunt dissection separates the desired tissues into separate areas, there is often a need to maintain the separation of those tissues. In fact, post surgical adhesions can occur following almost any type of surgery, resulting in serious postoperative complications. Adhesions may cause intestinal obstruction, bowel torsion, pain and infertility following general abdominal and pelvic surgery. Adhesions can also develop following orthopedic and cardiac surgery. Surgical adhesion disease is a complex inflammatory disease in which tissues that normally remain separated in the body grow into each other as a result of surgical trauma. Conventional surgical methods make use of anti-adhesion barriers, such as INTERCEED from Johnson & Johnson or SEPRAFILM from Genzyme Corporation.

INTERCEED is a fabric relatively easy to apply and handle. However, effectiveness may be diminished when bleeding has not been completely controlled. SEPRAFILM is widely used in general surgery. However, it is challenging for surgeons to apply and handle because of the film's tendency to easily break apart upon exposure to water due to their chemical make up and bio-dissolvable properties. The composition and structural properties of these bio-dissolvable products require that they be handled with dry hands or instruments, which can be difficult during most surgical intervention operations. Furthermore, many of these bio-dissolvable films are made intentionally thin to minimize tissue disruption and consequently end up being structurally weak (i.e., easily torn or folded during handling). In addition, SEPRAFILM is composed of two chemically modified biopolymers, sodium hyaluronate (HA) and carboxymethylcellulose (CMC), reacted with an activating agent 1-(3-dimethylaminopropyl)-3-ethylcarbodiimide hydrochloride (EDC) to form a water insoluble powder, hyaluronic acid-carboxymethylcellulose (HA-CMC). Although it is biodegradable, some of its breakdown products, such as smaller CMC units and ethyl-(3-dimethylaminopropyl)-urea (EDU), are not consumable by the patient's cell tissues. Hence, biodegradable substances, such as polymers, can cause inflammatory response due to either the parent substance or those substances formed during breakdown, and they may or may not be absorbed by tissues.

Another drawback of most barrier films is their non-elastic properties due to their sheet-like construction. In other words, the barrier films are not mechanically stretchable. Hence, it is difficult to use the barrier films to conform to three-dimensional surface of a tissue.

SUMMARY OF THE INVENTION

The present invention relates to a bio-absorbable stand-alone film that has one or more perforations or depressions provided in the film structure, and the corresponding method of making. The perforations in the bio-absorbable stand-alone film allow the film to expand and conform to a three-dimensional surface of a tissue, even in embodiments where the bio-absorbable film itself is not elastic. The bio-absorbable stand-alone film is generally formed of a naturally occurring oil, or an oil composition formed in part of a naturally occurring oil. In addition, the oil composition can include a therapeutic agent component, such as a drug or other bioactive agent. The perforations in the bio-absorbable film can speed up the biological absorption of the film by allowing body fluids to contact a greater amount of surface area of the film compared to a film without perforations. The bio-absorbable stand-alone film is implantable in a patient for short term or long term applications. As implemented herein, the bio-absorbable stand-alone film is a non-polymeric cross-linked gel derived at least in part from a fatty acid compound.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In accordance with one embodiment of the present invention, a bio-absorbable stand-alone film includes a film structure having a first side and a second side and formed of a non-polymeric cross-linked gel material formed at least in part of a fatty acid compound or derivative or analog thereof, and one or more perforations provided in the film structure.

In accordance with aspects of the present invention, the fatty acid compound includes omega-3 fatty acid, fish oil fatty acid, free fatty acid, triglycerides, esters of fish oil, or a combination thereof. The fish oil fatty acid can include one or more of arachidic acid, gadoleic acid, arachidonic acid, eicosapentaenoic acid, docosahexaenoic acid or derivatives, analogs and pharmaceutically acceptable salts thereof. The free fatty acid can include one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof.

In accordance with further aspects of the present invention, the bio-absorbable stand-alone film further includes a vitamin E compound forming a portion of the fatty acid compound. The vitamin E compound can include one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta tocotrienol succinate, delta-tocotrienol succinate, gamma-tocotrienol succinate, mixed tocopherols, vitamin E TPGS, derivatives, analogs and pharmaceutically acceptable salts thereof.

In accordance with further aspects of the present invention, the fatty acid compound or derivative or analog thereof is cured to increase viscosity to form the film. The bio-absorbable stand-alone film is cured using at least one curing method selected from a group of curing methods including application of UV light, application of heat, airflow, and reaction with a gas or chemical cross-linker. It should be noted that curing with respect to the present invention generally refers to thickening, hardening, or drying of a material brought about by heat, UV, or chemical means.

In accordance with further aspects of the present invention, the bio-absorbable stand-alone film further includes a therapeutic agent. The therapeutic agent can include an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the therapeutic agent is combined with the fatty acid compound prior to formation of the film, resulting in the therapeutic agent being interspersed throughout the film. Alternatively, the therapeutic agent is applied to the film in the form of a coating.

In accordance with further aspects of the present invention, the bio-absorbable stand-alone film is bioabsorbable. The bio-absorbable stand-alone film can further maintain anti-adhesive properties.

In accordance with further aspects of the present invention, the one or more perforations form a regular pattern. At least one of the one or more perforations may be a slit that is cut through the film from the first side through to the second side, or vice versa. The one or more perforations may have regular shapes. At least one of the one or more perforations may include a cavity for holding a liquid. The cavity may instead be adapted to hold one or more solid particles. Alternatively, the cavity may also be adapted to contain liquid with a solid particle. At least one of the one or more perforations may create an opening in the film adapted to allow a body part to pass through the film. The opening may be instead adapted to allow a surgical instrument to pass through the film without damaging the film. The opening in the film may be adapted to allow a fluid to pass through the film without damaging the film. In accordance with a further aspect of the present invention, at least one of the one or more perforations is disposed on the first side and/or the second side and does not pass completely through the film.

In accordance with further aspects of the present invention, the stand-alone film may further include a first coating disposed on the first side of the film. A second coating may be disposed on top of at least a portion of the first coating. Alternatively, the second coating may be disposed on the second side of the film. The first coating and/or the second coating may penetrate at least one of the one or more perforations. The first coating may cover only a portion of the first surface or the entire first surface.

In accordance with further aspects of the present invention, the stand-alone film is sterilized. The stand-alone film may also be packaged.

In accordance with another embodiment of the present invention, a method of making a stand-alone film is introduced. The method includes providing a non-porous stand-alone film having a first side and a second side and formed of a non-polymeric cross-linked gel material formed at least in part of a fatty acid compound or derivative or analog thereof. The method also includes forming at least one perforation in the film.

In accordance with one aspect of the present invention, the at least one perforation is formed by cutting, carving, puncturing, or other perforation forming action. In accordance with another aspect of the present invention, the at least one perforation penetrates completely through the film from the first side to the second side or vice versa. In accordance with yet another aspect of the present invention, the at least one perforation is disposed on the first side or the second side and does not pass completely through the film. In still another aspect of the present invention, the at least one perforation creates a cavity in the film.

In accordance with further aspects of the present invention, the method further includes filling the cavity with a liquid, solid, gas or combination thereof. The method may also include sterilizing and packaging the film. The process of sterilizing and packaging the film may include providing a pouch having a non-permeable chamber and a gas-permeable header, placing the film in the pouch, sealing the pouch along the gas-permeable header, such that the non-permeable chamber remains accessible through the gas-permeable header, sterilizing the film with a sterilizing agent provided through the gas-permeable header to the non-permeable chamber, sealing the film in the non-permeable chamber within the pouch, and optionally removing the header, leaving the film packaged within the non-permeable chamber and sterilized. In one embodiment, the sterilizing agent is selected from the group consisting of ethylene oxide (ETO) gas, radiation using gamma or electron-beam radiation, steam, gas plasma and vaporized hydrogen peroxide.

In accordance with one aspect of the present invention, the method optionally includes purging the pouch with an inert gas prior to sealing the non-permeable chamber and removing the gas-permeable header after the gas permeable header is sealed. The inert gas can comprise argon or nitrogen. In accordance with another aspect of the present invention, the method optionally includes exposing the pouch to vacuum conditions and purging the pouch with an inert gas prior to sealing the gas permeable header. The inert gas can comprise argon or nitrogen. In accordance with yet another aspect of the present invention, after the film is placed in the pouch, the method optionally includes purging the pouch with an inert gas and exposing the pouch to vacuum conditions prior to sealing the gas permeable header. The inert gas can comprise argon or nitrogen.

In accordance with further aspects of the present invention, prior to sealing the gas permeable header, a desiccant, an oxygen scavenger, an oxygen barrier, or a combination thereof is added to the pouch. The desiccant is selected from the group consisting of silica gel, clay, molecular sieves, potassium permanganate, activated carbon, activated alumina, and a water absorbable polymer.

In accordance with a further embodiment of the present invention, a stand-alone film including a film structure having a first side and a second side and formed of a non-polymeric cross-linked gel material formed at least in part of a fatty acid compound or derivative or analog thereof and one or more depressions molded in the film structure on the first side and/or the second side is provided. At least one of the one or more depressions may not pass completely through the film. Alternatively, at least one of the one or more depressions may penetrate completely through the film from the first side to the second side, or vice versa. The stand-alone film may further include a coating disposed on the first surface and/or the second surface. The stand-alone film may also be sterilized and/or packaged.

In accordance with yet another embodiment of the present invention, a method of making a stand-alone film is provided. The method includes providing a compound in liquid form and being a non-polymeric material formed at least in part of a fatty acid compound or derivative or analog thereof; applying the compound to a mold having one or more protrusions; and curing the compound to form the stand-alone film having a first side and a second side.

In accordance with one aspect of the present invention, the one or more protrusions may create one or more depressions on the first side of the stand-alone film. Alternatively, the one or more protrusions may create one or more holes in the stand-alone film.

In accordance with further aspects of the present invention, the method may further includes providing a pouch having a non-permeable chamber and a gas-permeable header; placing the film in the pouch; sealing the pouch along the gas-permeable header, such that the non-permeable chamber remains accessible through the gas-permeable header; sterilizing the film with a sterilizing agent provided through the gas-permeable header to the non-permeable chamber; sealing the film in the non-permeable chamber within the pouch; and optionally removing the header, leaving the film packaged within the non-permeable chamber and sterilized. The sterilizing agent may be selected from the group consisting of ethylene oxide (ETO) gas, radiation using gamma or electron-beam radiation, steam, gas plasma and vaporized hydrogen peroxide. After the film is placed in the pouch, the method may further include the steps of exposing the pouch to vacuum conditions and purging the pouch with an inert gas prior to sealing the gas permeable header. The inert gas may include argon or nitrogen. Alternatively, after the film is placed in the pouch, the method may further include the steps of purging the pouch with an inert gas and exposing the pouch to vacuum conditions prior to sealing the gas permeable header, where the inert gas includes argon or nitrogen.

BRIEF DESCRIPTION OF THE DRAWINGS

The present invention will become better understood with reference to the following description and accompanying drawings, wherein:

FIG. 1A is an exemplary illustration of a bio-absorbable stand-alone film with cut through perforations forming a regular pattern according to one embodiment of the present invention;

FIG. 1B is an exemplary top-view illustration of a bio-absorbable stand-alone film with circular-shaped perforations forming an irregular pattern in accordance with one embodiment of the present invention;

FIG. 1C is an exemplary top-view illustration of a bio-absorbable stand-alone film with irregular-shaped perforations forming circular patterns in accordance with one embodiment of the present invention;

FIG. 1D is an exemplary top-view illustration of a bio-absorbable stand-alone film with two cut through perforations forming a cross shape in accordance with one embodiment of the present invention;

FIG. 1E is an exemplary top-view illustration of a bio-absorbable stand-alone film with a perforation that creates an opening in the film structure in accordance with one embodiment of the present invention;

FIG. 1F is an exemplary top-view and blow-up view illustrations of a bio-absorbable stand-alone film with a perforation that creates a cavity in the film in accordance with one embodiment of the present invention;

FIG. 1G is an exemplary top-view illustration of a bio-absorbable stand-alone film with perforations or depressions in accordance with one embodiment of the present invention;

FIG. 1H is a side view illustration of the film in FIG. 1G when the film is cut along the AA' line in accordance with one embodiment of the present invention;

FIG. 2B shows a perforated stand-alone film conforming to a three-dimensional surface of a tissue, in accordance with another embodiment of the present invention;

DETAILED DESCRIPTION

Figure 2A:
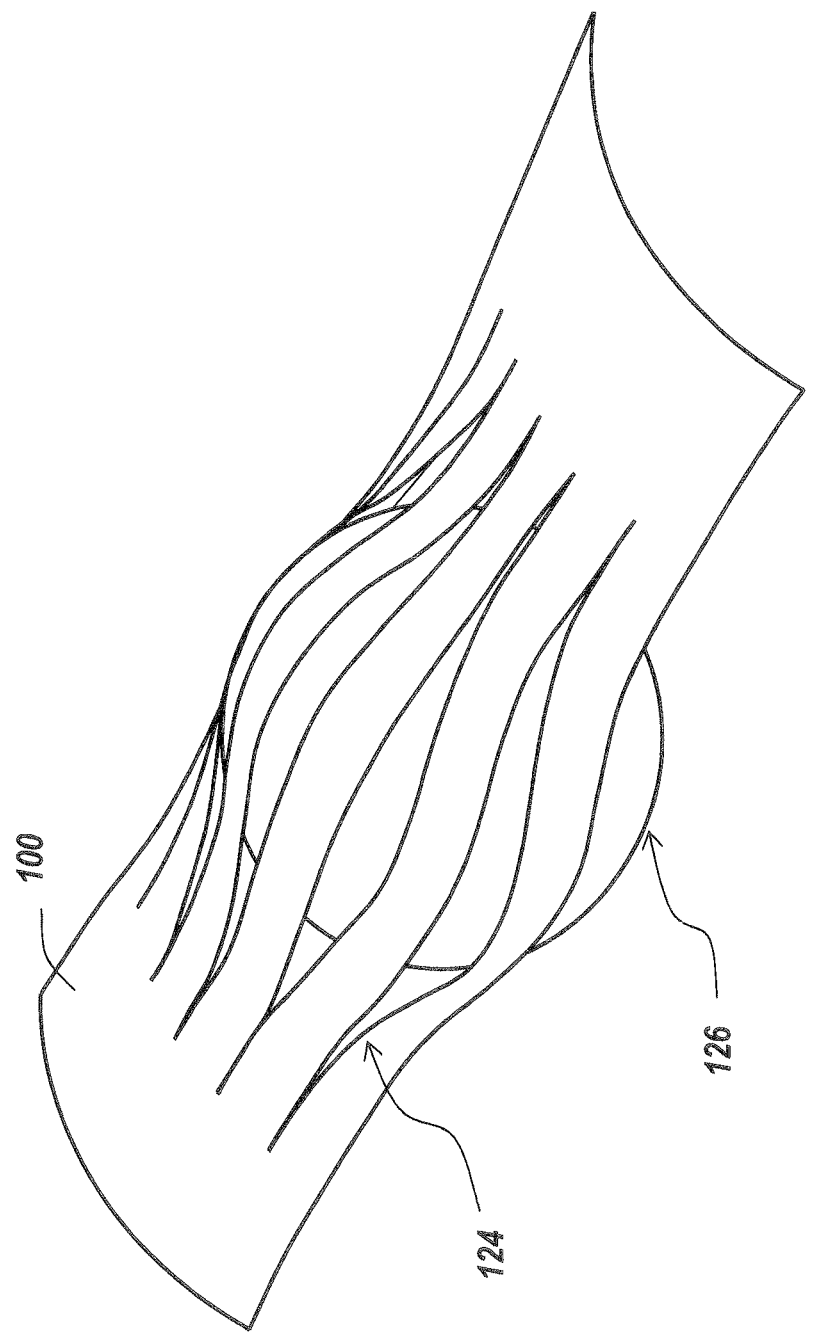
FIG. 2A shows a perforated stand-alone film conforming to a three-dimensional surface of a tissue, in accordance with one embodiment of the present invention.

The present invention utilizes primarily fatty acids to form a bio-absorbable stand-alone film. One or more perforations or depressions are formed in the film. The phrase stand-alone film is used herein to refer to a film that does not require any material in addition to the film material to provide structure to the film. A medical device having a coating of fish oil is not a stand-alone film because the coating of fish oil relies on the device to provide structure to the film. The perforations in the bio-absorbable stand-alone film allow the film to expand and conform to a three-dimensional surface of a tissue even in instances where the bio-absorbable film is non-elastic. The stand-alone films are bioabsorbable and cells may consume the breakdown products, fatty acid, short and long chain alcohol, and glyceride molecules. Bioabsorbable substances break down into substances or components that do not cause an inflammatory response and can be consumed by the cells forming the body tissues. The perforations in the bio-absorbable film also help the biological absorption of the film by allowing body fluids to contact a greater amount of surface area of the film compared to a film without perforations. Furthermore, the resultant film is flexible, easy to handle, and relatively strong. The resultant film may be used with many surgical procedures when anti-adhesion is desirable for a pre-determined amount of time.

FIGS. 1A through 9 illustrate example embodiments of a non-polymeric bio-absorbable stand-alone film with perforations or depressions formed therein and the method of making according to the present invention. FIG. 1A illustrates an exemplary bio-absorbable stand-alone film 100 according to one embodiment of the present invention. The bio-absorbable stand-alone film 100 has a first side 102 and a second side 104. The bio-absorbable stand-alone film 100 is flexible, to the extent that it can be placed in a flat, curved, or rolled configuration within a patient. The stand-alone-film 100 is implantable, for both short term and long term applications. The bio-absorbable stand-alone film 100 has a thickness in the range of 0.003 inches to 0.008 inches. One of ordinary skill in the art will appreciate that thicker films may be made from layering several bio-absorbable stand-alone films 100 together, or the film itself may be made thicker. In other words, the thicker the bio-absorbable stand-alone film 100 is, the longer it takes for the bio-absorbable stand-alone film 100 to completely breakdown in the patient's body. The bio-absorbable stand-alone film 100 may be constructed to provide a barrier for a predetermined period of time, such as, but not limited to, a period of hours, a period of weeks, or a period of months.

Bio-absorbable stand-alone film 100 is made from fatty acids, such as omega-3 fatty acid, fish oil fatty acid, free fatty acid, triglycerides, esters of fish oil, or a combination thereof. Fish oil fatty acid may further be one or a combination of arachidic acid, gadoleic acid, arachidonic acid, eicosapentaenoic acid, docosahexaenoic acid or derivatives, analogs, and pharmaceutically acceptable salts thereof. Free fatty acid may be one or more of butyric acid, caproic acid, caprylic acid, capric acid, lauric acid, myristic acid, palmitic acid, palmitoleic acid, stearic acid, loeic acid, vaccenic acid, linoleic acid, alpha-linolenic acid, gamma-linolenic acid, behenic acid, erucic acid, lignoceric acid, or derivatives, analogs and pharmaceutically acceptable salts thereof.

More specifically, the bio-absorbable stand-alone film 100 is formed of a non-polymeric cross-linked gel derived from fatty acid compounds. The fatty acids include omega-3 fatty acids when the oil utilized to form the bio-absorbable stand-alone film is fish oil or an analog or derivative thereof. As liquid fish oil is heated, autoxidation occurs with the absorption of oxygen into the fish oil to create hydroperoxides in an amount dependent upon the amount of unsaturated (C=C) sites in the fish oil. However, the (C=C) bonds are not consumed in the initial reaction. Concurrent with the formation of hydroperoxides is the isomerization of (C=C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the film after the (C=C) bonds have substantially isomerized into the trans configuration. The (C=C) bonds can also form C—C cross-linking bridges in the glyceride hydrocarbon chains using a Diels-Alder Reaction. In addition to solidifying the film through cross-linking, both the hydroperoxide and (C=C) bonds can undergo secondary reactions converting them into lower molecular weight secondary oxidation byproducts including aldehydes, ketones, alcohols, fatty acids, esters, lactones, ethers, and hydrocarbons.

Accordingly, the film derived from fatty acid compounds, such as those of fish oil, includes a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the film. The film degrades into fatty acid, short and long chain alcohol, and glyceride molecules, which are all non-inflammatory and likewise consumable by cells in the soft tissue to which the film is applied. Thus, the film is bioabsorbable.

The bio-absorbable stand-alone film 100 further provides a lubricious and anti-adhesive surface against tissue. The bio-absorbable stand-alone film itself, in its substantially cured configuration, can provide a physical anti-adhesion barrier between two sections of tissue. The use of the naturally occurring oil, such as fish oil, provides extra lubrication to the surface of the film, which helps to reduce injury. With less injury, there is less of an inflammatory response, and less healing required. The oily surface of the film provides the anti-adhesion characteristics. One of ordinary skill in the art will appreciate that different oils will have different anti-adhesive properties, and the oils can be modified to be more liquefied or more solid or waxy, as desired. Accordingly, the degree of anti-adhesive properties offered by the film can vary. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature conditions and/or increasing UV output, more cross-links form transitioning the gel from a relatively liquid gel to a relatively solid-like, but still flexible, gel structure.

In accordance with one aspect of the present invention, the bio-absorbable stand-alone film 100 can further include a therapeutic agent. The therapeutic agent can include an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics. The therapeutic agent may be added to the fatty acid compound prior to forming a bio-absorbable stand-alone film so that the therapeutic agent is interspersed throughout the bio-absorbable stand-alone film 100. Alternatively, the therapeutic agent may be applied to the bio-absorbable stand-alone film 100 to form a coating on a surface of the bio-absorbable stand-alone film after the fatty acid compound has formed a bio-absorbable stand-alone film.

In accordance with one aspect of the present invention, the therapeutic agent can include a vitamin E compound. The vitamin E compound may include one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

One of ordinary skill in the art will appreciate that the bio-absorbable stand-alone film of the present invention may be applied with other therapeutic agents that are not listed above. These therapeutic agents are added for healing purposes and not to provide structure to the bio-absorbable stand-alone film. Furthermore, the bio-absorbable stand-alone film can be formed in a manner that creates the potential for controlled long term release of a therapeutic agent, while still maintaining the benefits of the natural oil component of the film. With the present invention, and in the field of soft tissue applications, the uptake of the therapeutic agent is facilitated by the delivery of the therapeutic agent to the cell membrane by the bio-absorbable stand-alone film.

The bio-absorbable stand-alone film 100 can be formed with many different kinds of perforations or depressions. In accordance with one aspect of the present invention, the bio-absorbable stand-alone film 100 may have perforations 106 that are slits that are cut through the film from the first side through to the second side or vice versa. The perforations 106 form a regular pattern and are lined up with one another. The perforations 106 create slits with the same length. The distance between any two adjacent perforations is also the same.

In accordance with another aspect of the present invention, the stand-alone film may have perforations 108 that create small holes in the film as shown in FIG. 1B. The perforations 108 have regular shapes-circles. The perforations may or may not be of the same size. The perforations 108 may or may not form a regular pattern, but in the present example are positioned randomly.

In accordance with yet another aspect of the present invention, the stand-alone film may have perforations 110 as shown in FIG. 1C. The perforations 110 have irregular shapes, but they form regular patterns in the form of circles.

In accordance with still another aspect of the present invention, the stand-alone film may have multiple perforations that intersect or overlap with one another, such as shown in FIG. 1D. Perforations 112 are two slits that intersect each other. The slits are cut through from the first side 102 to the second side 104. Such an arrangement may allow instruments to be inserted through the film when needed, but still maintains relative good separation of tissues from both sides of the film. Alternatively, the perforations may also allow a body part to pass through the film when needed. An advantage of such perforations is that the perforations are adaptable to create openings of different sizes in the film when needed but still allow the film to maintain its barrier function without creating a big opening in the film.

In accordance with yet another aspect of the present invention, the stand-alone film as shown in FIG. 1E may have a perforation 114 creating an opening that is big enough to allow a surgical instrument to pass through the film without damaging the film. The opening can also be adapted to allow a body part to pass through the film. The opening can also be adapted to allow a fluid to pass through the film without damaging the film.

In accordance with still another embodiment of the present invention, the stand-alone film as shown in FIG. 1F has perforations 116 that include a cavity. The cavity has an opening 120 and a compartment 118. The opening 120 is on one surface of the film and the compartment 118 is between the first surface 102 and the second surface 104 of the film. In other words, the cavity does not penetrate from one side of the film to the other. The cavity may be used to hold a liquid in the compartment 118. The cavity may also be used to hold one or more solid particles in the compartment 118. The cavity may hold both liquid and solid particles.

In accordance with yet another embodiment of the present invention, the stand-alone film as shown in FIG. 1G has perforations 122 that are only disposed on the first side 102 and/or the second side 104 and do not pass completely through the film. The perforations 122 have regular shapes, but in this instance they do not form a regular pattern, although a pattern is possible. Alternatively, perforations 122 may be viewed as depressions 122 that form only on the surface and do not penetrate through the film. FIG. 1H illustrates a side view from line AA' in FIG. 1G. FIG. 1H better illustrates that perforation/depression 122 does not penetrate through one side of the film to the other.

One of ordinary skill in the art will appreciate that the present invention is not limited to the specific shapes and dimensions that are disclosed herein and the illustrative embodiments are merely for demonstration purposes only. Specifically, locations, patterns, placement, size, shape, depth, and other variations of the perforations, as would be understood by one of ordinary skill in the art are possible.

FIG. 2A illustrates how a perforated stand-alone film can be used to conform to a three-dimensional surface of a tissue in accordance with one embodiment of the present invention. Perforated stand-alone film 100 has narrow slits 124 as perforations. The perforations 124 allow the stand-alone film 100 to expand in a manner that is not possible with the prior art non-elastic barrier films. Perforated stand-alone film 100 is able to conform to a three-dimensional surface of a tissue 126 without tearing the film 100. This is achieved with the perforations 124 because they provide points or areas of expansion in an otherwise non-expandable or non-elastic material. The perforations 124 create openings in the film to allow body fluids to pass through the film and accelerate the bio-absorption process of the film by a patient's body.

FIG. 2B illustrates how a perforated stand-alone film can be used to conform to a three-dimensional surface of a tissue in accordance with another embodiment of the present invention. Bio-absorbable stand-alone film 100 has perforations 124 that allow the film 100 to wrap around a three-dimensional surface 126 of a tissue. One of ordinary skill in the art will appreciate that there are many different perforation configurations and orientations that the stand-alone film 100 can have so that it can conform to various tissue surfaces. The perforations in a stand-alone film also accelerate the degradation of the film due to its greater amount of surface area compared to a stand-alone film of the same size without any perforations. Hence, a perforated stand-alone film is capable of conforming to a three-dimensional surface of a tissue, and can also accelerate the bio-absorption of the film by a patient's body.

Figure 3A:
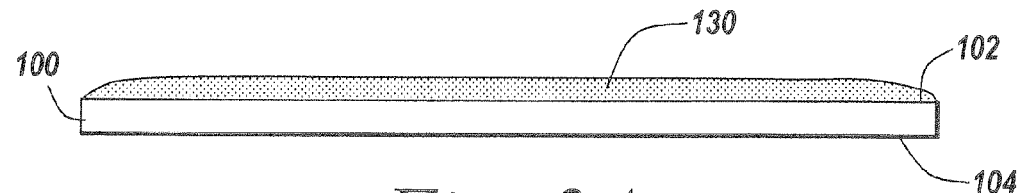
FIG. 3A is an exemplary side view illustration of a stand-alone film covered with a coating on one side of the film in accordance with one embodiment of the present invention.
Figure 3B:
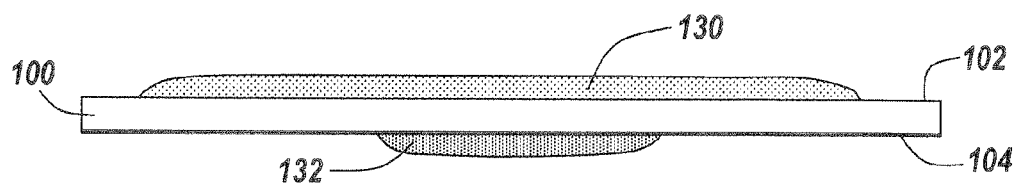
FIG. 3B is an exemplary side view illustration of a stand-alone film covered with a coating on both sides of the film in accordance with one embodiment of the present invention.
Figure 3C:
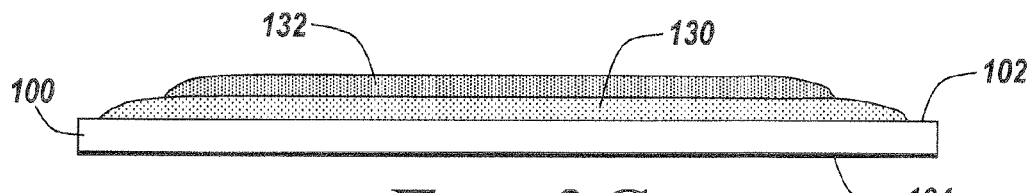
FIG. 3C is an exemplary side view illustration of a stand-alone film covered with two coatings on one side of the film in accordance with one embodiment of the present invention.
Figure 3D:
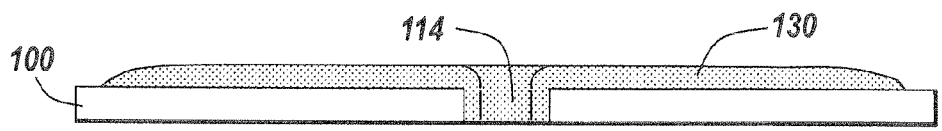
FIG. 3D is an exemplary side view illustration of a stand-alone film covered with a coating on one side of the film in accordance with one embodiment of the present invention, where the coating penetrates a perforation formed within the film.
Figure 3E:
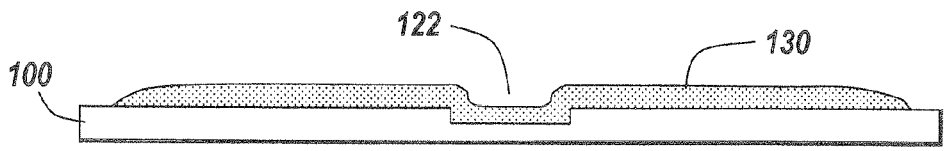
FIG. 3E is an exemplary side view illustration of a stand-alone film covered with a coating on one side of the film in accordance with one embodiment of the present invention, where the coating covers a depression formed within the film.

In accordance with further aspects of the present invention, the stand-alone film may have a coating on one side or both sides of the film. As shown in FIG. 3A, the stand-alone film 100 has a coating 130 disposed on the first side 102 of the film. The coating 130 may cover a portion of the first surface or the entire first surface. In FIG. 3B, the stand-alone film 100 may have a second coating 132 disposed on the second surface 104, in addition to the first coating 130 disposed on the first surface 102. In this illustration, the second coating 132 covers only a portion of the second surface 104, however one of ordinary skill in the art will appreciate that the second coating 132 may alternatively cover the entire second surface 104. In FIG. 3C, the stand-alone film 100 has a second coating 132 disposed on top of at least a portion of the first coating 130. One of ordinary skill in the art will appreciate that further coatings may be applied on the first surface 102 and/or the second surface 104 of the film 100. In FIG. 3D, the first coating 130 penetrates a perforation 114. One of ordinary skill in the art will appreciate that the first coating can also be applied and not to penetrate the perforation 106. In FIG. 3E, the first coating 130 covers a depression 122 of the stand-alone film 100. One of ordinary skill in the art will appreciate that the first coating 130 can alternatively not cover the depression 122 of the film 100 or the depression 122 may be covered by a different coating. One of ordinary skill in the art will appreciate that there are many different configurations of what portions of the film are covered by a coating.

The types of coatings on the stand-alone film are not particularly limited and can include, for example, biodegradable and non-biodegradable coatings; polymeric coatings such as polyethylene coatings; non-polymeric coatings, bioabsorbable coatings, and the like. Accordingly, coatings on the stand-alone film may be chemically sensitive, or may include chemically sensitive components or therapeutics. In accordance with one embodiment of the present invention, the coating can be in the form of a non-polymeric cross-linked gel.

In one embodiment, the coatings can be any of the above-mentioned coatings with or without one or more therapeutic agents. The therapeutic agents suitable for use in the invention are not particularly limited. The therapeutic agents can be hydrophilic, lipophilic, amphiphilic or hydrophobic, and can be dissolved in the bio-absorbable carrier, the solvent or the bio-absorbable carrier and the solvent. The therapeutic agent can be any agent having therapeutic value when administered to a subject, for example, a mammal.

As utilized herein, the phrase "therapeutic agent(s)" refers to a number of different drugs or agents available, as well as future agents that may be beneficial for use with the bio-absorbable stand-alone film of the present invention. The therapeutic agent can take a number of different forms including but not limited to anti-oxidants, anti-inflammatory agents, anti-coagulant agents, drugs to alter lipid metabolism, anti-proliferatives, anti-neoplastics, tissue growth stimulants, analgesics, functional protein/factor delivery agents, anti-infective agents, anti-imaging agents, anesthetic agents, therapeutic agents, tissue absorption enhancers, anti-adhesion agents, anti-migratory agents, pro-healing agents, ECM/Protein production inhibitors, germicides, antiseptics, proteoglycans, GAG's, gene delivery (polynucleotides), polysaccharides (heparin), rapamycin, melatonin, paclitaxel, a protein kinase C inhibitor, cerivastatin, cilostazol, fluvastatin, lovastatin, pravastatin or derivatives, analogs, prodrugs and pharmaceutically acceptable salts thereof, and any additional desired therapeutic agents such as those listed in Table 1 below.

TABLE 1

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |

TABLE 1-continued

| CLASS | EXAMPLES |
|---|---|
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibitation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example as described in US Patent Application Publication 2004/0235762), a rapamycin derivative (for example, as described in U.S. Pat. No. 6,200, 985), everolimus, seco-rapamycin, seco-everolimus, and simvastatin.

For drug loading, a therapeutic agent is combined with a fatty acid compound prior to formation of the film in accordance with one embodiment of the present invention. Hence, the resultant film has the therapeutic agent interspersed throughout the film. For drug coating, a therapeutic agent is applied in the form of a coating on a bio-absorbable stand-alone film. In one embodiment, a coating can be applied by overlaying a drug-loaded fatty acid compound on a bio-absorbable stand-alone film. After a therapeutic agent is dissolved in an appropriate solvent, it is blended with a fatty acid compound to form a coating material. The solvent is evaporated prior to applying the coating material as a coating on a bio-absorbable stand-alone film. Alternatively, the therapeutic agent may be blended directly into the fatty acid compound without the use of a solvent. The coating material can be, for example, sprayed or brushed onto a bio-absorbable stand-alone film. The coating material can also be cast directly on top of a bio-absorbable stand-alone film. The bio-absorbable stand-alone film with the coating material is heated or exposed to UV light to raise the viscosity of the coating material beyond the gelation point and hence create a cross-linked gel coating on the bio-absorbable stand-alone film. Alternatively, the coating material can be left in a state of lower viscosity to preserve drug recovery rate or to alter the release characteristics of the therapeutic agent used in the coating material.

Figure 4:
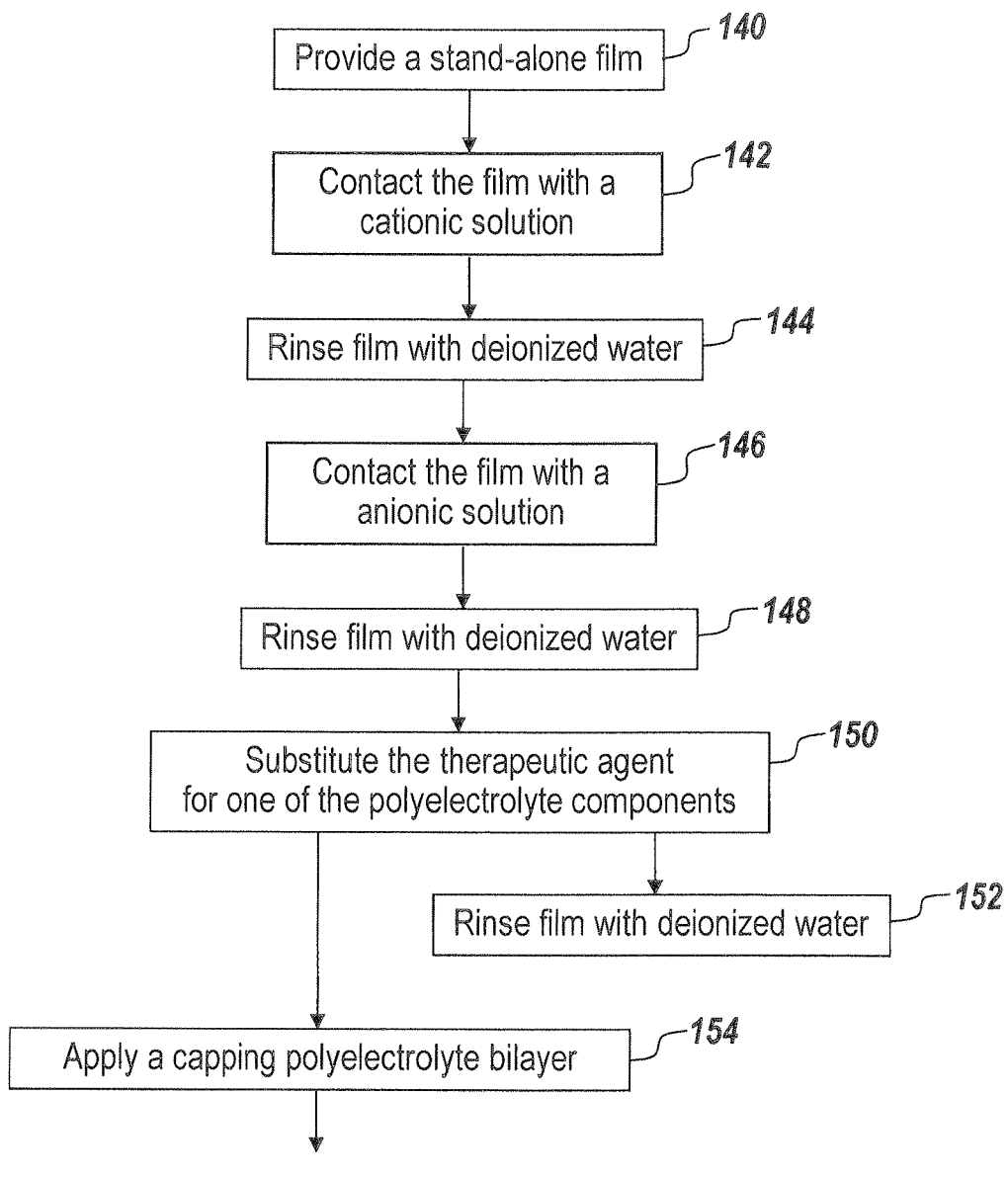
FIG. 4 is a flow chart illustrating a method of coating a stand-alone film according to one embodiment of the present invention.

In accordance with one embodiment of the present invention, a coating can be applied using a polyionic layer-by-layer (LBL) technique as shown by the flow chart in FIG. 4. After a bio-absorbable stand-alone film 100 is provided (step 140), the bio-absorbable stand-alone film is contacted by a cationic solution (+charged) for a period of time (step 142), after which the bio-absorbable stand-alone film is rinsed with deionized water (step 144). This results in the bio-absorbable stand-alone film being added with a layer of positively charged polyelectrolyte coating. Another layer of coating is then applied by contacting the bio-absorbable stand-alone film with an anionic solution (− charged) for a period of time (step 146), after which the bio-absorbable stand-alone film is again rinsed with deionized water (step 148). One or ordinary skill in the art will appreciate that the concentration of the polyelectrolytes can be varied. A therapeutic agent is coated onto the bio-absorbable stand-alone film by substituting the therapeutic agent for one of the polyelectrolyte components of the LBL system (step 150). After the therapeutic agent is applied, the bio-absorbable stand-alone film may be rinsed with deionized water (step 152). Using this general procedure, a single drug layer can be coated on the surface of the bio-absorbable stand-alone film. Alternatively, a capping polyelectrolyte bilayer can be applied after the drug is coated onto the surface of the bio-absorbable stand-alone film (step 154) and the procedure (steps 148, 150, and 154) can be repeated several times to create multiple buried drug layers.

Figure 5:
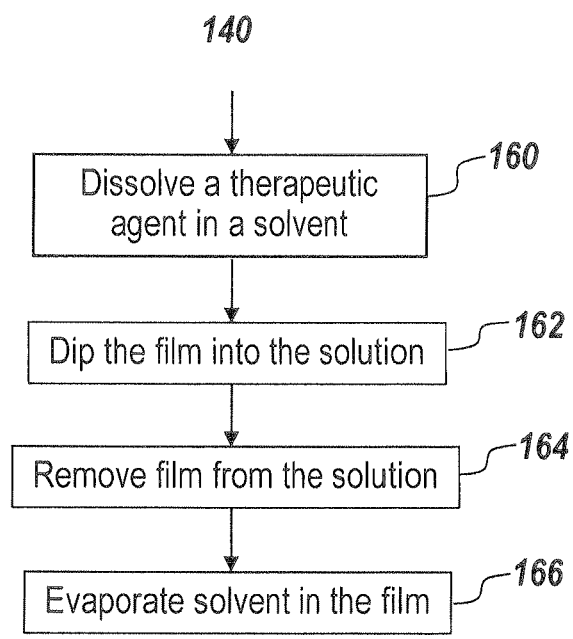
FIG. 5 is a flow chart illustrating an alternative method of coating a stand-alone film according to one embodiment of the present invention.

In accordance with yet another embodiment of the present invention, a coating can be applied by dipping a bio-absorbable stand-alone film in a solvent-therapeutic mixture to load the therapeutic agent onto the bio-absorbable stand-alone film as shown by the flow chart in FIG. 5. A therapeutic agent is dissolved in an appropriate solvent (step 160). The bio-absorbable stand-alone film is then dipped into the solution for a period of time to coat the surface of the film or to allow the film to swell and absorb some of the solution (step 162). The bio-absorbable stand-alone film is then removed (step 164) and the solvent in the film is evaporated (step 166). Examples of solvents that may be used with this method include, but are not limited to, ethanol and nMP.

One of ordinary skill in the art will appreciate that there are other methods, such as spraying or painting, to apply a coating on a stand-alone film other than the ones listed above. One of ordinary skill in the art will also appreciate that the coatings may or may not have a therapeutic agent incorporated therein. The stand-alone film may be initially made without a therapeutic agent and later a coating with a therapeutic agent can be applied to the film. The types of therapeutic agents used in the film and the coatings may or may not be the same. For example, the perforated stand-alone film may have a longer acting agent processed into the film whereas the coatings may have a shorter acting agent.

Figure 6:
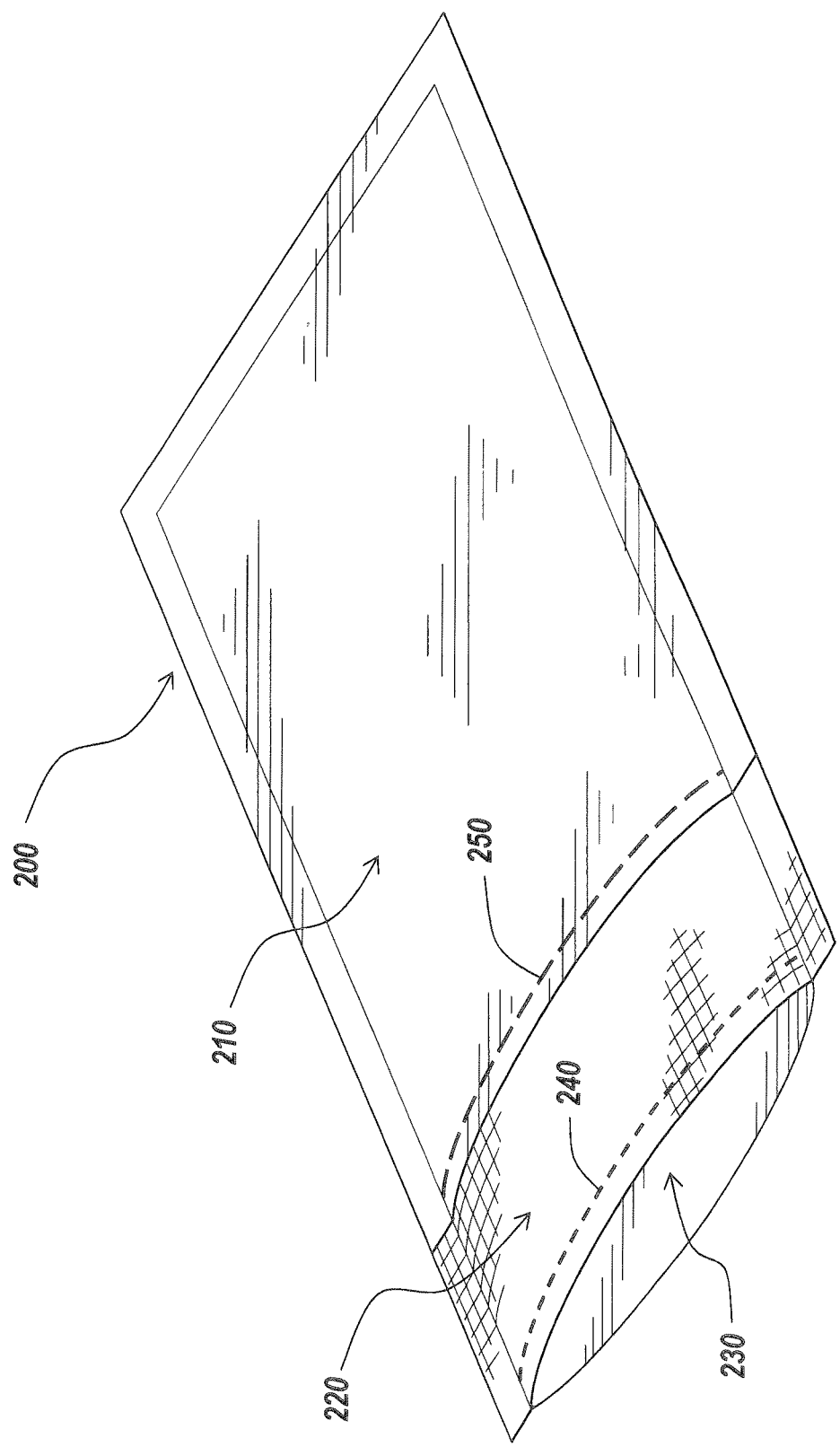
FIG. 6 is a diagrammatic illustration of a packaging pouch with a header, in accordance with one aspect of the present invention.

In accordance with another aspect of the present invention, the film may be sterilized or packaged. FIG. 6 is a diagrammatic illustration of a packaging pouch with a non-permeable chamber and a gas permeable header, where the pouch may be used to sterilize and/or package the film. In accordance with one aspect of the present invention, the packaging pouch 200 is comprised of a non-permeable material 210 and gas permeable header 220. The permeable material may be composed of a material such as TYVEK. The material is permeable to the extent of allowing permeation of the material by sterilization gases or products, as described herein. The packaging pouch has a chamber 230 capable of containing a variety of stand-alone films. Appropriate stand-alone films for use with the present invention include, for example, implantable stand-alone films (i.e., stents, balloons, catheters, stand alone films, surgical mesh, and the like), surgical instruments (i.e., forceps, scalpels, retractors and the like); and any other stand-alone film or instrument in need of sterilization. In addition, the packaging pouch can be manufactured in any size and/or shape to contain any manner of stand-alone film or instrument.

Referring again to FIG. 6, the packaging pouch has two sites to seal the pouch for sterilization. A first sealing site 240 is located at the opening of the pouch at the top of the gas permeable header 220. A second sealing site 250 is located at the bottom of the header 120.

One of ordinary skill in the art will appreciate that the packaging pouch 200 is merely one example illustrative embodiment of the packaging structure that can be used in accordance with the present invention. For example, the header 220 can be implemented in a number of different structural embodiments, so long as the functional aspects of the header as described herein, including its permeability to the desired sterilization and inert gases, is maintained. The header 220 can be implemented as a patch, access point, valve, or other gas permeable implementation that performs in a similar manner as the header described herein with regard to the sterilization methodology of the present invention. The header 220 can be disposed at any location on the packaging that enables the method of sterilization.

Furthermore, the material 210 of the packaging can be made of a number of different materials, so long as the functionality of being non-permeable, or substantially non-permeable to air is maintained. For example, plastics, composites, metals, and other materials can provide this functionality.

In addition, one of ordinary skill in the art will appreciate that the present invention is not limited with respect to the location of the seals (the first sealing site 240 and the second sealing site 250), and the specific configuration illustrated and described herein. The seals can be configured and located in a number of different implementations, so long as the seals provide the functionality of sealing off a chamber that includes the gas permeable area (e.g. header 220) and then subsequently sealing off the foil material 210 area of the packaging pouch 200 so that the sterilized contents of the packaging pouch 200 is maintained in its sterile environment.

It should be noted that the sterilization occurs without substantially degrading the chemically sensitive stand-alone film, or any coatings applied to the stand-alone film or any therapeutic agents contained in the coatings. In one embodiment, the sterilization does not substantially alter the coating through the loss of cis double bonds or by altering the degree of cross-linking of the coating.

Figure 7:
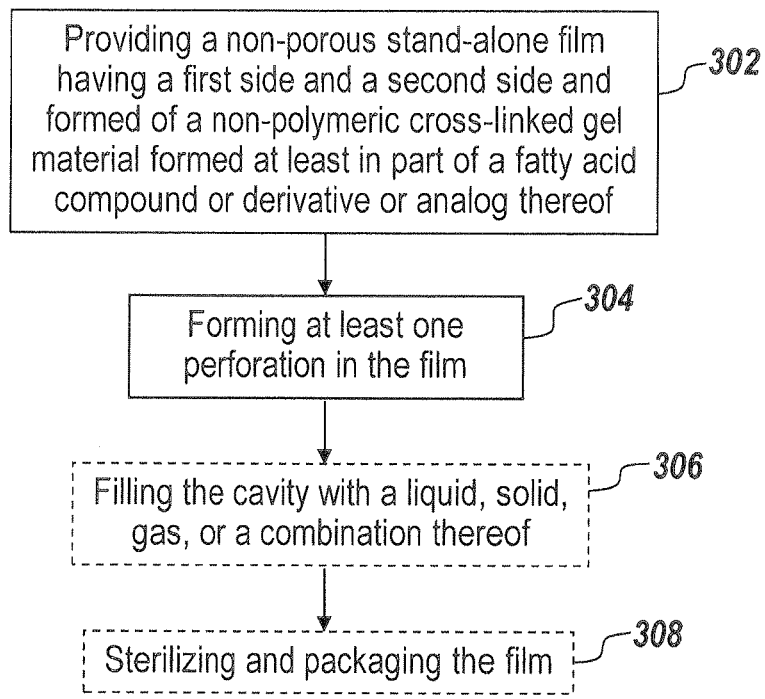
FIG. 7 is a flow chart illustrating a method of making a stand-alone film with one or more perforations according to one embodiment of the present invention.

FIG. 7 is a flow chart illustrating a method of creating a stand-alone film with one or more perforations in the film structure. In accordance with one aspect of the present invention, a non-porous stand-alone film having a first side and a second side and formed of a non-polymeric cross-linked gel material formed at least in part of a fatty acid compound or derivative or analog thereof is provided (step 302). At least one perforation (106, 108, 110, 112, 114, 116, 122) in then formed in the film (step 304). The at least one perforation (106, 108, 110, 112, 114, 116, 122) can be formed by cutting, carving, or puncturing the film. The at least one perforation (106, 108, 110, 112, 114) can completely penetrate through the film from the first side to the second side or vice versa. Alternatively, the at least one perforation (110, 116, 122) can also be disposed on the first side and/or the second side and does not pass completely through the film. The at least one perforation (116) may create a cavity (118) in the film. The cavity (118) can be optionally filled with a liquid, solid, gas, or a combination thereof (step 306). The film can then be optionally sterilized and packaged (step 308).

Figure 8:
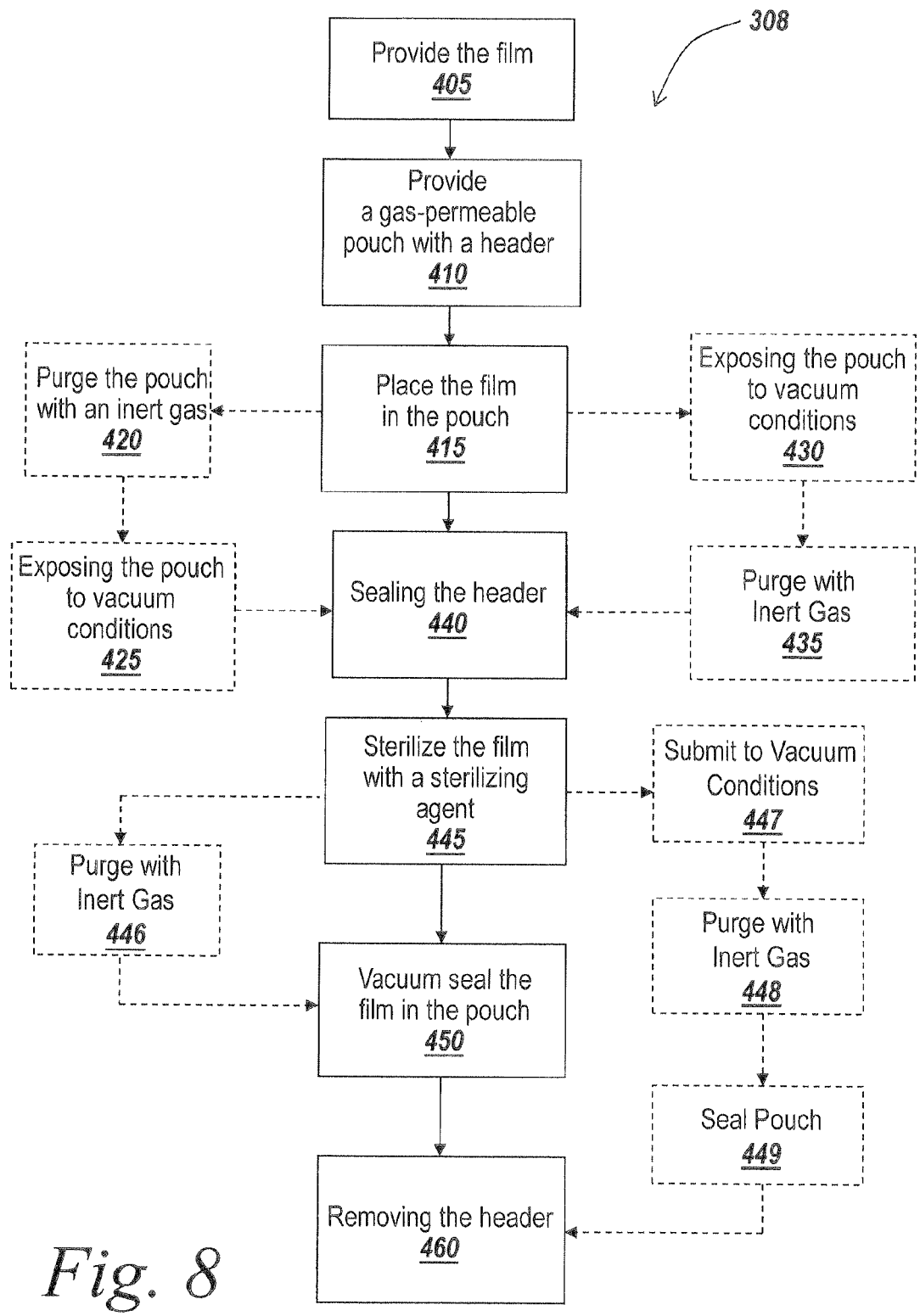
FIG. 8 is a flow chart illustrating a method of packaging and sterilizing a bio-absorbable stand-alone film, in accordance with one aspect of the present invention.

FIG. 8 is flow chart illustrating the detailed steps of packaging and sterilizing a chemically sensitive stand-alone film with a sterilizing agent in step 308. In accordance with one aspect of the present invention, a chemically sensitive stand-alone film 100 is provided (step 405). As used herein, the term "chemically sensitive" refers to any material that may degrade and/or chemically react upon exposure to heat, steam, water, air or a chemical, or a combination thereof. A chemically sensitive stand-alone film 100 can be a device in which one or more components of the device may degrade and/or chemically react upon exposure to heat, steam, water, air or a chemical or a combination thereof. Chemically sensitive components of the stand-alone film can include, for example, any material that comprises the device itself, as well as any coatings and/or therapeutic agents comprised within the coatings or the stand-alone film.

Still referring to FIG. 8, a packaging pouch 200 is provided (step 410). The stand-alone film 100 is then placed in the packaging pouch 200 (step 415). In accordance with one aspect of the present invention, a desiccant, an oxygen scavenger, an oxygen barrier, or a combination thereof may be added to the packaging pouch 200 before the pouch is sealed. Suitable desiccants include, for example, silica gel, clay, molecular sieves, potassium permanganate, activated carbon, and activate alumina. Suitable oxygen scavengers include any inorganic material that can absorb oxygen, for example, iron oxide powders, sulfites, bisulfites, butylated hydroxytoluene (BHT), butylated hydroxyanisole (BHA), oxygen absorbable polymers enclosed in a pouch or added inside the packaging (e.g., Chevron-Phillips Chemical Company's ethylene methylacrylate cyclohexene methyl acrylated (EMCM) polymer or Ciba's Specialty Chemical's SHELFPLUS. Examples of oxygen barriers include, for example, polyvinylidene chloride (PVDC)-coated films and polyvinyl alcohol (PVOH). In one embodiment, the antioxidant and/or the desiccant material may be incorporated into the material that is used to make the pouch. In another embodiment, the packaging pouch may be comprised of an antioxidant packaging material. Examples of antioxidant packaging material include, for example, ethylene methylacrylate cyclohexene methyl acrylated (EMCM) polymer (Chevron-Phillips), Ciba Specialty Chemicals SHELFPLUS or other commercially available antioxidant packaging material. In yet another embodiment, the packaging material may optionally be gas permeable.

In one embodiment, the pouch can be purged with inert gas (step 420), then submitted to vacuum conditions (step 425) before sealing of the gas permeable header (step 440). In another embodiment, the pouch can be submitted to vacuum conditions (step 430), then purged with an inert gas (Step 435) prior to the sealing of the gas permeable header (step 440). In yet another embodiment, the pouch containing the stand-alone film is sealed at the opening of the pouch at the top of the header (step 440) upon placing the stand-alone film in the pouch. Upon sealing at this point, the packaging pouch is permeable to gasses and vapors in order to allow a sterilization process to occur.

The sealed pouch 200 containing the stand-alone film 100 is then sterilized with a sterilizing agent (step 445). Sterilizing agents are well known in the art and can include, for example, normal ethylene oxide (ETO) gas, cold ETO gas, aqueous glutaraldehyde solution, radiation using gamma or electron-beam radiation and steam, gas plasma, and vaporized hydrogen peroxide (VHP). In one particular embodiment, the sterilizing agent is vaporized hydrogen peroxide. In another particular embodiment, the sterilizing agent is cold ETO gas in which the ETO gas is administered at about 25-130° C. In another embodiment, the ETO gas is administered at about 37° C. Accordingly, a stand-alone film with a coating and optionally containing one or more therapeutic agents, upon sterilization with VHP or cold ETO gas, has diminished degradation of the stand-alone film, the coating and/or the one or more therapeutic agents. Furthermore, upon sterilization, the shelf life of the stand-alone film is extended.

Referring still to FIG. 8, after sterilization of the stand-alone film 100 in the packaging pouch 200, the non-permeable chamber is then vacuum sealed (step 450) at point 250. In accordance with one example embodiment of the present invention, the packaging pouch 200 can be purged with an inert gas, such as argon or nitrogen, prior to vacuum sealing of the non-permeable chamber at the second sealing point 250 (step 446). The packaging pouch is vacuum sealed at the second sealing point 250. After the packaging pouch is vacuum sealed at sealing point 250, the header can then be removed (step 460), if desired. In accordance with another embodiment of the present invention, the sterile packaging pouch can be subjected to vacuum conditions (step 447), purged with an inert gas, for example, argon or nitrogen (step 448) and sealed (step 449) at the second sealing point 250. After the packaging pouch is sealed, the header can then be removed (step 460), if desired.

Figure 9:
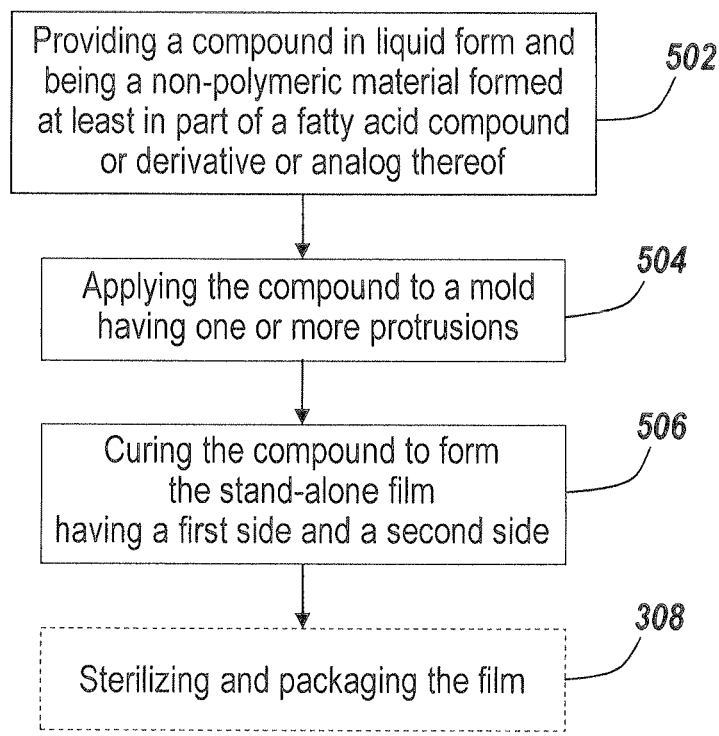
FIG. 9 is a flow chart illustrating a method of making a stand-alone film with one or more depressions according to one embodiment of the present invention.

FIG. 9 is a flow chart illustrating another method of the present invention, in the form of making a stand-alone film 100 with one or more depressions 122. In accordance with one aspect of the present invention, a compound in liquid form and being a non-polymeric material formed at least in part of a fatty acid compound or derivative or analog thereof is provided (step 502). The compound is then applied to a mold having one or more protrusions (step 504). The compound is cured on the mold to form the stand-alone film 100 having a first side 102 and a second side 104 (step 506). The one or more protrusions create one or more depressions 122 on the first side or the second side of the stand-alone film. The one or more protrusions can alternatively create one or more holes in the stand-alone film 100. The one or more protrusions may or may not have the same size, shape, width, or height. Hence, it is possible to use a mold to create a stand-alone film that has both a depression and a hole. Lastly, the film may be optionally sterilized and packaged in step 308.

The perforated bio-absorbable stand-alone film 100 of the present invention may be used as a barrier to keep tissues separated to avoid adhesion. Application examples for adhesion prevention include abdominal surgeries, spinal repair, orthopedic surgeries, tendon and ligament repairs, gynecological and pelvic surgeries, and nerve repair applications. The perforated bio-absorbable stand-alone film may be applied over the trauma site or wrapped around the tissue or organ to limit adhesion formation. The addition of therapeutic agents to the bio-absorbable stand-alone films used in these adhesion prevention applications can be utilized for additional beneficial effects, such as pain relief or infection minimization. Other surgical applications of the bio-absorbable stand-alone film may include using a bio-absorbable stand-alone film as a dura patch, buttressing material, internal wound care (such as a graft anastomotic site), and internal drug delivery system. The perforated bio-absorbable stand-alone film may also be used in applications in transdermal, wound healing, and non-surgical fields. The perforated bio-absorbable stand-alone film may be used in external wound care, such as a treatment for burns or skin ulcers. The perforated bio-absorbable stand-alone film may be used without any therapeutic agent as a clean, non-permeable, non-adhesive, non-inflammatory, anti-inflammatory dressing, or the perforated bio-absorbable stand-alone film may be used with one or more therapeutic agents for additional beneficial effects. The perforated bio-absorbable stand-alone film may also be used as a transdermal drug delivery patch when the perforated bio-absorbable stand-alone film is loaded or coated with one or more therapeutic agents. The perforations in the bio-absorbable stand-alone film allow the film to expand and conform to a three-dimensional surface of a tissue even if the bio-absorbable film is non-elastic. The perforations in the bio-absorbable film also help the biological absorption of the film by allowing body fluids to contact a greater amount of surface area of the film compared to a film without perforations.

The process of wound healing involves tissue repair in response to injury and it encompasses many different biologic processes, including epithelial growth and differentiation, fibrous tissue production and function, angiogenesis, and inflammation. The cross-linked gel used to make the inventive bio-absorbable stand-alone film has been shown in an animal model not to produce an inflammatory response, but still provide excellent cellular overgrowth with little to no fibrous capsule formation. Accordingly, the bio-absorbable stand-alone film provides an excellent material suitable for wound healing applications.

The present invention provides methods for making bio-absorbable stand-alone films with perforations or depressions. The bioabsorbable nature of the stand-alone film results in the film being completely absorbed over time by the cells of the body tissue. There is no breakdown of the bio-absorbable stand-alone film into components and substances that are known to be inflammatory and are eventually distributed throughout the body and in some instances disposed of by the body, as in the case with biodegradable synthetic polymer surgical films. In addition, the bio-absorbable stand-alone film surface can be made to be either lubricious or anti-adhesive against body tissues. The fatty acid derived cross-linked gel that makes up the bio-absorbable stand-alone film can be made to exhibit minimal to no anti-inflammatory reaction to localized tissue or be made to exhibit non-inflammatory properties by use of one or more therapeutic agents in the film itself, or its coating. Selection of biological oil blends, with or without medication, can be made to influence the amount of inflammation, which in selected localized tissue applications can reduce, minimize or alter naturally occurring adhesions following blunt tissue dissection. A perforated bio-absorbable stand-alone film made from fatty acid compounds is flexible, easy to handle, and can be shaped easily as a result of its improved conformability. One or more therapeutic agents may be applied to the perforated bio-absorbable stand-alone film or by use of one or more therapeutic loaded coatings. Hence, the bio-absorbable stand-alone film not only provides improved bio-mechanical performance to an inelastic biological film material, but further enhances the biological delivery mechanism when therapeutic agents are desired.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the disclosed invention is reserved.

What is claimed is:

1. A method of making a stand-alone film, said method comprising:
   providing a non-porous stand-alone film having a first side and a second side and formed of a non-polymeric cross-linked gel material formed at least in part of a fatty acid compound or derivative or analog thereof;
   forming one or more perforations in the film;
   wherein at least one of the one or more perforations comprises a slit that passes through the film from the first side through to the second side, or vice versa.

2. The method of claim 1, wherein the one or more perforations is formed by cutting.

3. The method of claim 1, wherein the one or more perforations are formed by carving.

4. The method of claim 1, wherein the one or more perforations are formed by puncturing.

5. The method of claim 1, wherein the one or more perforations create a cavity in the film.

6. The method of claim 5, further comprising filling the cavity with a liquid, solid, gas or combination thereof.

7. The method of claim 1, further comprising sterilizing and packaging the film.

8. The method of claim 7, further comprising:
   providing a pouch having a non-permeable chamber and a gas-permeable header;
   placing the film in the pouch;
   sealing the pouch along the gas-permeable header, such that the non-permeable chamber remains accessible through the gas-permeable header;
   sterilizing the film with a sterilizing agent provided through the gas-permeable header to the non-permeable chamber;
   sealing the film in the non-permeable chamber within the pouch; and
   optionally removing the header, leaving the film packaged within the non-permeable chamber and sterilized.

9. The method of claim 8, wherein the sterilizing agent is selected from the group consisting of ethylene oxide (ETO) gas, radiation using gamma or electron-beam radiation, steam, gas plasma and vaporized hydrogen peroxide.

10. The method of claim 8, wherein after the gas permeable header is sealed, the method further comprises the step of purging the pouch with an inert gas prior to sealing the non-permeable chamber and removing the gas permeable header.

11. The method of claim 10, wherein the inert gas comprises argon or nitrogen.

12. The method of claim 8, wherein after the film is placed in the pouch the method further comprises the steps of:
   exposing the pouch to vacuum conditions; and
   purging the pouch with an inert gas prior to sealing the gas permeable header.

13. The method of claim 12, wherein the inert gas comprises argon or nitrogen.

14. The method of claim 8, wherein after the film is placed in the pouch, the method further comprises the steps of:
   purging the pouch with an inert gas; and
   exposing the pouch to vacuum conditions prior to sealing the gas permeable header.

15. The method of claim 14, wherein the inert gas comprises argon or nitrogen.

16. The method of claim 8, wherein prior to the sealing the gas permeable header, a desiccant, an oxygen scavenger, an oxygen barrier, or a combination thereof is added to the pouch.

17. The method of claim 16, wherein the desiccant is selected from the group consisting of silica gel, clay, molecular sieves, potassium permanganate, activated carbon, activated alumina, and a water absorbable polymer.

* * * * *